United States Patent
Dunshee

[19]

[11] Patent Number: 6,018,092

[45] Date of Patent: Jan. 25, 2000

[54] MEDICAL ADHESIVE BANDAGE, DELIVERY SYSTEM AND METHOD

[75] Inventor: Wayne K. Dunshee, Maplewood, Minn.

[73] Assignee: 3M Innovative Properties Company, St. Paul, Minn.

[21] Appl. No.: 08/810,584

[22] Filed: Mar. 4, 1997

[51] Int. Cl.[7] .................................................. A61F 13/02
[52] U.S. Cl. ............................... 602/54; 602/57; 602/58; 602/59; 206/440; 206/441
[58] Field of Search .................................. 206/440, 441; 602/41–59

[56] References Cited

U.S. PATENT DOCUMENTS

| | | | |
|---|---|---|---|
| Re. 24,906 | 12/1960 | Ulrich | 206/59 |
| Re. 32,010 | 10/1985 | Collins | 156/527 |
| Re. 33,727 | 10/1991 | Sims . | |
| 1,643,926 | 9/1927 | Dickson | 602/440 |
| 2,292,995 | 8/1942 | Greenwoll . | |
| 2,308,693 | 1/1943 | Goldman | 28/80 |
| 2,401,714 | 6/1946 | Weil . | |
| 2,465,876 | 3/1949 | Hornung | 206/16 |
| 2,508,855 | 5/1950 | Brown | 28/74 |
| 2,529,060 | 11/1950 | Trillich | 117/68.5 |
| 2,587,928 | 3/1952 | Tuck et al. | 312/39 |
| 2,627,341 | 2/1953 | Morgan | 206/441 |
| 2,887,247 | 5/1959 | Williams, Jr. | 221/25 |
| 2,897,961 | 8/1959 | Bush | 206/63.2 |
| 3,025,854 | 3/1962 | Scholl | 602/57 |
| 3,085,024 | 4/1963 | Blackford | 117/4 |
| 3,143,208 | 8/1964 | Sizemore, Jr. | 206/56 |
| 3,389,827 | 6/1968 | Abere et al. | 220/53 |
| 3,520,403 | 7/1970 | Moshel | 206/63.2 |
| 3,530,494 | 9/1970 | Baratta | 206/63.2 |
| 3,630,346 | 12/1971 | Burnside | 206/56 |
| 3,835,992 | 9/1974 | Adams, IV | 206/390 |
| 3,899,077 | 8/1975 | Spiegelberg | 206/441 |
| 4,017,002 | 4/1977 | Doyle et al. | 221/63 |
| 4,112,177 | 9/1978 | Salditt et al. | 428/304 |
| 4,112,213 | 9/1978 | Waldman | 526/279 |
| 4,194,624 | 3/1980 | Speigelberg | 206/441 |
| 4,265,234 | 5/1981 | Schaar | 128/156 |
| 4,298,647 | 11/1981 | Cancio et al. | 428/167 |
| 4,310,509 | 1/1982 | Berglund et al. | 424/28 |
| 4,323,557 | 4/1982 | Rosso et al. | 424/28 |
| 4,336,097 | 6/1982 | Van Kampen et al. | 156/527 |

(List continued on next page.)

FOREIGN PATENT DOCUMENTS

| | | |
|---|---|---|
| 0 051 935 A2 | 5/1982 | European Pat. Off. . |
| 0 066 899 A2 | 12/1982 | European Pat. Off. . |
| 0 081 990 A1 | 5/1983 | European Pat. Off. . |
| 1002738 | 3/1952 | France . |
| 1047563 | 12/1953 | France ............ 19/2 |
| 2 409 210 | 11/1977 | France ........ B65D 75/30 |
| 2 012 362 | 9/1971 | Germany ........ A61F 15/06 |
| 38 21 698 | 1/1990 | Germany ........ A61F 13/02 |
| 3821 698 A1 | 1/1990 | Germany . |
| 59-214449 | 12/1984 | Japan . |
| 704214 | 2/1954 | United Kingdom . |
| 886474 | 1/1962 | United Kingdom . |
| 2 120 104 A | 11/1983 | United Kingdom . |
| WO 89/11262 | 11/1989 | WIPO . |
| WO 95/18046 | 7/1995 | WIPO . |
| 95/18046 | 7/1997 | WIPO ............... 206/441 |

*Primary Examiner*—Richard J. Apley
*Assistant Examiner*—Kim M. Lee
*Attorney, Agent, or Firm*—Gary L. Griswold; Eloise J. Maki; Stephen W. Bauer

[57] ABSTRACT

A medical adhesive bandage and delivery system including a medical adhesive bandage and a package. The bandage has a backing, an adhesive on a first surface of the backing, and a pad proximate the first surface of the backing. At least one line of separation (for example, a line of perforations) is provided in the backing and the pad to facilitate selective manual separation of the bandage into more than one bandage. The package may include a release area or liner, with the adhesive on the medical adhesive bandage releasably adhered to the release area or liner. The package preferably tends to retain the bandage therein when the package is torn and the bandage is separated along a line of separation.

44 Claims, 5 Drawing Sheets

U.S. PATENT DOCUMENTS

| | | | |
|---|---|---|---|
| 4,346,700 | 8/1982 | Dunshee et al. | |
| 4,380,564 | 4/1983 | Cancio et al. | 428/167 |
| 4,465,729 | 8/1984 | Cancio et al. | 428/167 |
| 4,472,480 | 9/1984 | Olson | 428/332 |
| 4,499,896 | 2/1985 | Heinecke | |
| 4,505,770 | 3/1985 | Larimore | 156/235 |
| 4,526,166 | 7/1985 | Silber | |
| 4,549,653 | 10/1985 | Lauritzen | 206/441 |
| 4,562,102 | 12/1985 | Rabuse et al. | 428/43 |
| 4,581,087 | 4/1986 | Johnson | 156/209 |
| 4,595,001 | 6/1986 | Potter et al. | 128/156 |
| 4,600,001 | 7/1986 | Gilman | |
| 4,666,040 | 5/1987 | Murata | 206/441 |
| 4,737,393 | 4/1988 | Linkoes | 428/43 |
| 4,737,410 | 4/1988 | Kanter | 428/343 |
| 4,759,652 | 7/1988 | Ulrich | 401/196 |
| 4,772,499 | 9/1988 | Greenway | 428/43 |
| 4,787,380 | 11/1988 | Scott | |
| 4,807,753 | 2/1989 | Goldstein | 206/390 |
| 4,837,062 | 6/1989 | Dunshee et al. | 428/41 |
| 4,882,213 | 11/1989 | Goddia et al. | 428/136 |
| 4,915,102 | 4/1990 | Kwiatek et al. | |
| 4,917,929 | 4/1990 | Heinecke | 428/41 |
| 4,947,567 | 8/1990 | Hermann | 40/299 |
| 4,993,586 | 2/1991 | Taulbee et al. | 221/25 |
| 5,102,008 | 4/1992 | Kaufman et al. | 221/25 |
| 5,114,771 | 5/1992 | Ogg et al. | 428/43 |
| 5,133,477 | 7/1992 | Etheredge, III et al. | 221/25 |
| 5,160,315 | 11/1992 | Heinecke et al. | 602/57 |
| 5,198,276 | 3/1993 | Nakajima | 428/43 |
| 5,213,565 | 5/1993 | Rollband | 602/41 |
| 5,230,701 | 7/1993 | Meyer et al. | 602/76 |
| 5,242,725 | 9/1993 | Weissmann et al. | 428/40 |
| 5,271,522 | 12/1993 | Ko et al. | 221/58 |
| 5,397,297 | 3/1995 | Hunter | 602/54 |
| 5,413,567 | 5/1995 | Barth et al. | 604/307 |
| 5,496,605 | 3/1996 | Augst et al. | 428/43 |
| 5,511,689 | 4/1996 | Frank | 221/73 |

MEDICAL ADHESIVE BANDAGE, DELIVERY SYSTEM AND METHOD

FIELD OF THE INVENTION

The present invention relates to the field of medical adhesive bandages. More particularly, the present invention provides a medical adhesive bandage, delivery system for dispensing medical adhesive bandages in incremental lengths as needed by the user, and methods of using the same.

BACKGROUND OF THE INVENTION

Medical adhesive bandages typically include a backing, an absorbent pad, and a pressure sensitive adhesive to maintain the medical adhesive bandage in place. As referred to below, "bandage" or "bandages" will be understood to refer to medical adhesive bandages. The bandages are typically used to cover cuts, scrapes and other skin conditions. They are typically packaged individually to maintain cleanliness of the bandages before use. As an added benefit, the individual packaging also provides the opportunity to provide bandages that are sterile until removed from the packaging. Typically, however, sterility of the bandages is only a secondary concern to the primary requirement that the bandages be clean and free of foreign matter before application.

The individual packaging of the bandages, however, results in a number of disadvantages. Packaging the bandages individually increases their cost. It can also increase the waste generated when the bandages are used. Another disadvantage is that the size of the bandage is fixed, i.e., if a wound is larger than the bandage, the user must obtain a larger bandage or open a number of individually packaged bandages to cover the wound. At the opposite end of the size problem is that the wound may be significantly smaller than bandages available to the user and, as a result, use of the bandage may be wasteful because a smaller bandage would be sufficient to cover the wound.

One attempt at providing user-sized bandages has involved providing a roll-form bandage having a continuous backing and continuous length absorbent pad. The user removes the roll from a box or other storage device, cuts a bandage of the desired length from the roll and replaces the roll in the box. In addition to providing opportunities for contamination of the roll if improperly handled, this delivery system requires the user to obtain and use scissors or another cutting instrument to separate a bandage from the roll.

Another attempt involved providing an approximately 10 centimeter long backing and associated pad in sheet from that is packaged in a box or envelope. To obtain a bandage having the desired size, the user removes the sheet bandage from the package, cuts off a piece having the desired size, and replaces the remaining portion of the sheet bandage back in the package. Like the bandages dispensed from a roll, the handling and storage of the larger sheet bandage provides opportunities for contamination if improperly handled and also requires the user to obtain and use a scissors or other cutting device to separate a bandage from the sheet.

Another attempt involved providing a foam tape perforated at 0.5 inch (1.27 centimeter) intervals across the tape and placing absorbent pads on the tape between the perforations to provide bandages that could be individually dispensed by separating the tape along the lines of perforation. This material was also provided in roll form in a box or other storage device. To dispense a bandage, the user removed the roll from the box or other storage device, cut or tore (along a line of perforations) a bandage of the desired length from the roll and replaced the roll in the box. As discussed above, the handling and storage of the bandages in roll-form provided opportunities for contamination of the remaining material because the pads were exposed both during storage and dispensing. Another problem with this delivery system was the difficulty in accurately placing the pads between the lines of perforation. If the pads crossed the perforation lines, it was difficult to tear the tape along the lines of perforation and, in addition, the pad edges would fray.

SUMMARY OF THE INVENTION

The present invention provides a medical adhesive bandage delivery system that provides for the dispensing of medical adhesive bandages in sizes desired by a user while protecting the remaining portion of the medical adhesive bandage from exposure to foreign matter. The present invention preferably does so by providing a medical adhesive bandage that is releasably attached to the packaging material such that it is retained substantially within the packaging material until dispensed.

In one aspect, the present invention provides a medical adhesive bandage delivery system including a medical adhesive bandage having a backing, an adhesive on a first surface of the backing, a pad proximate the first surface of the backing, at least one line of separation in the backing and the pad; and a package having a top sheet having an inner surface and an outer surface, a bottom sheet having an inner surface and an outer surface, and a release area on the inner surface of the bottom sheet of the package, wherein the adhesive on the medical adhesive bandage is releasably adhered to the release area.

In another aspect, the present invention provides a medical adhesive bandage delivery system including a medical adhesive bandage having a backing, an adhesive on a first surface of the backing, a pad proximate the first surface of the backing, at least one line of perforations in the backing and the pad; and a package including a top sheet having an inner surface and an outer surface, a bottom sheet having an inner surface and an outer surface, and a release liner attached to the inner surface of the bottom sheet of the package, the release liner including at least one line of separation formed therein, wherein the bond strength between the release liner and the inner surface of the bottom sheet is greater than the bond strength between the adhesive on the medical adhesive bandage and the release liner.

In another aspect, the present invention provides a medical adhesive bandage delivery system including a medical adhesive bandage having a backing, an adhesive on a first surface of the backing, at least one line of separation in the backing, and a plurality of pads proximate the first surface of the backing, the plurality of pads being generally aligned along a length of the backing, wherein one of the at least one line of separation is located between each adjacent pair of the plurality of pads; and a package having a top sheet having an inner surface and an outer surface, a bottom sheet having an inner surface and an outer surface, and a release area on the inner surface of the bottom sheet of the package, wherein the adhesive on the medical adhesive bandage is releasably adhered to the release area.

In another aspect, the present invention provides a medical adhesive bandage delivery system including a medical adhesive bandage having a backing, an adhesive on a first surface of the backing, at least one line of perforations in the backing, and a plurality of pads proximate the first surface of the backing, the plurality of pads being generally aligned along a length of the backing, wherein one of the at least one line of perforation is located between each adjacent pair of the plurality of pads; and a package having a top sheet having an inner surface and an outer surface, a bottom sheet having an inner surface and an outer surface, and a release liner on the inner surface of the bottom sheet of the package, the release liner including at least one line of perforations formed therein, wherein the bond strength between the release liner and the inner surface of the bottom sheet is greater than the bond strength between the adhesive on the medical adhesive bandage and the release liner.

In yet another aspect, the present invention provides a method of delivering a medical adhesive bandage including steps of providing a medical adhesive bandage delivery system comprising a medical adhesive bandage having a backing, an adhesive on a first surface of the backing, a pad proximate the first surface of the backing, and at least one line of separation in the backing and the pad, wherein the medical adhesive bandage is packaged in a package comprising a top sheet having an inner surface and an outer surface, a bottom sheet having an inner surface and an outer surface, and a release area on the inner surface of the bottom sheet of the package, wherein the adhesive on the medical adhesive bandage is releasably adhered to the release area. The user then separates the package and the medical adhesive bandage along one of the at least one line of separation in the medical adhesive bandage, whereby the medical adhesive bandage delivery system is separated into first and second portions; separates the top and bottom sheets of the package in the first portion of the medical adhesive bandage delivery system; and removes the medical adhesive bandage from the release area on the bottom sheet of the package in the first portion of the medical adhesive bandage delivery system.

In a still further aspect, the present invention provides a medical adhesive bandage delivery system including a sheet having a plurality of medical adhesive bandages, each of the plurality of medical adhesive bandages comprising a backing, adhesive on a first surface of the backing, and a pad proximate the first surface of the backing, wherein adjacent pairs of the plurality of medical adhesive bandages are connected along a line of separation, a top sheet of packaging material having an inner surface and an outer surface, a bottom sheet of packaging material having an inner surface and an outer surface, and a release area on the inner surface of the bottom sheet of the packaging material, wherein the adhesive on each of the plurality of medical adhesive bandages is releasably adhered to the release area.

In yet another aspect, the present invention provides a medical adhesive bandage having a backing having a first surface, an adhesive on the first surface of the backing, a pad on the first surface of the backing, and at least one line of separation in the backing and pad to facilitate selective manual separation of the bandage into more than one bandage.

These and various other features and advantages of the present invention are described in more detail below.

DESCRIPTION OF THE PREFERRED EMBODIMENTS

Figure 1:
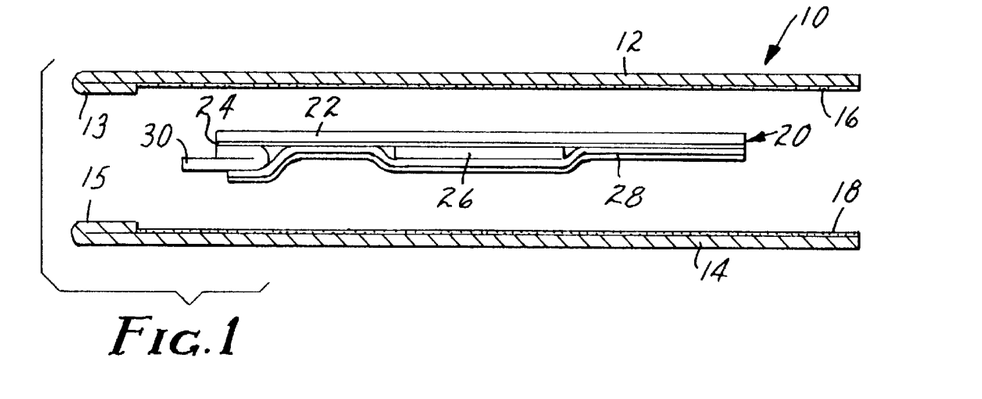
FIG. 1 is an exploded cross-sectional view of one medical adhesive bandage delivery system according to the present invention.

The medical adhesive bandage delivery system of the present invention is useful in connection with any medical adhesive bandage having a pressure-sensitive adhesive coating positioned on the backing surface. Referring now to FIG. 1, an exploded view of one medical adhesive bandage delivery system 10 according to the present invention is shown in cross-section. The medical adhesive bandage delivery system 10 includes a top sheet 12 of packaging material and a bottom sheet 14 of packaging material. Located between the sheets 12 and 14 of packaging material is one medical adhesive bandage 20. The medical adhesive bandage 20 includes a backing 22, adhesive 24 on one surface of the backing 22, and an absorbent pad 26 located on the adhesive 24. A liner 28 is provided to cover a majority of the exposed adhesive 24.

As shown in FIG. 1, the medical adhesive bandage 20 may also include a release tab 30 located on one end of the medical adhesive bandage 20. The release tab 30 facilitates removal of the medical adhesive bandage 20 from the bottom sheet 14 of the package and also aids in placing the medical adhesive bandage 20 on a patient. The depicted release tab 30 is a piece of liner material that has been folded once. Other variations in the design of release tabs for adhesive composites articles will be known to those skilled in the art.

Representative backing materials 22 include nonwoven fibrous webs, woven fibrous webs, knits, foams, films and other suitable backing materials. Whatever the backing material, it is preferably capable of forming relatively clean edges along a line of separation as discussed below.

It is also preferred, but not required, that the backing materials 22 be at least partially permeable to moisture vapor released through a patient's skin. In some instances, permeability can be obtained and/or increased by providing a number of openings in the backing material 22. One preferred type of backing material 22 is nonwoven urethane material, such as described in, for example, U.S. Pat. No. 5,230,701 to Meyer et al.

The preferred pressure sensitive adhesives 24 which can be used in the medical adhesive bandage 20 provided in connection with the present invention are the normal adhesives which are applied to the skin. Examples of useful adhesives include those described in U.S. Pat. No. 4,112,177 (particularly the tackified acrylate "skin layer adhesive" described in Example 1). Other suitable adhesives are described in U.S. Pat. No. 5,648,166. Additional suitable adhesives include the acrylate copolymers described in U.S. Pat. No. RE 24,906. Another example of a useful adhesive is an 70:15:15 isooctyl acrylate: ethyleneoxide acrylate-:acrylic acid terpolymer, as described in U.S. Pat. No. 4,737,410 (see Example 31). Other useful adhesives are described in U.S. Pat. Nos. 3,389,827, 4,112,213, 4,310,509, and 4,323,557. Inclusion of medicaments or antimicrobial agents in the adhesive is also contemplated, as described in U.S. Pat. Nos. 4,310,509 and 4,323,557.

The pressure sensitive adhesives 24 preferably transmit moisture vapor to increase patient comfort. While moisture vapor transmission can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001.

In the preferred embodiments according to the present invention, the choice of adhesives is limited to those that are safe to use on human or animal skin, and preferably to those that are of the class known as "hypoallergenic" adhesives. The preferred acrylate copolymers are adhesives of this class.

It will also be understood that the present invention may also include a barrier layer between the backing and adhesive as described in U.S. patent application Ser. No. 08/391, 658, titled ADHESIVE SHEET ARTICLES, filed Feb. 21, 1995.

Liner materials for the liner 28 are available from a variety of manufacturers in a wide variety of proprietary formulations. Those skilled in the art will normally test those liner materials in simulated use conditions against an adhesive of choice to arrive at a product with the desired release characteristics.

Release liners 28 that are suitable for use in the medical adhesive bandage delivery system 10 of the present invention can be made of kraft papers, polyethylene, polypropylene, polyester or composites of any of these materials. The release liner 28 preferably comprises release agents such as fluorochemicals or silicones. For example, U.S. Pat. No. 4,472,480, the disclosure of which is hereby incorporated by reference, describes low surface energy perfluorochemical liners. Some preferred liners 28 are papers, polyolefin films, or polyester films coated with silicone release materials. Examples of commercially available silicone coated release papers SILOX-coated release papers, available from the Akrosil Division of International Paper (Menasha, Wis.), and the silicone release papers supplied by Daubert Coated Products, Inc. (Willowbrook, Ill.).

Other combinations of adhesives 24 and release liners 28 are contemplated for use with embodiments according to the present invention. Those skilled in the art will be familiar with the processes of testing new combinations of adhesives 24 and release liners to arrive at the combination of qualities desired in a final product. The considerations pertinent to the selection of silicone release liners can be found in Chapter 18 of the Handbook of Pressure Sensitive Adhesive Technology Van Nostrand-Reinhold, 1982, pp. 384–403. U.S. Pat. No. 4,472,480 also describes considerations pertinent to the selection of a perfluoropolyether release liner.

As indicated above, the medical adhesive bandage 20 is located in a package having a top sheet 12 and bottom sheet 14. Although the top and bottom sheets 12 and 14 are depicted and described separately, it will be understood that they could be formed from a single sheet of material folded to form two sheets during manufacturing and assembly of the medical adhesive bandage delivery system.

The materials used for the packaging sheets 12 and 14 can be papers, polyethylene, polypropylene, polyester or composites of any of these materials. The primary requirements for the packaging materials are the ability to provide a sealable package and compatibility with sterilization processes. In addition, the materials used for the package must be easily torn and the line of tearing must generally propagate in a desired direction. In some instances it may be desirable to include tear strips or other guiding devices/coatings on or in the packaging material to assist in clean, linear tearing of the packaging material. It may also be desirable to use materials such as oriented fiber papers to assist in providing clean, linear edges in the packaging material where torn.

The top sheet 12 and bottom sheet 14 each preferably include a layer 16 and 18, respectively, of cohesive material on their respective facing or inner surfaces. The cohesive material forms a bond when activated, typically through pressure or pressure and heat. One example of a suitable cohesive material is described in U.S. Pat. No. 2,529,060. As a result, the areas of the top sheet 12 and bottom sheet 14 that are not separated by the medical adhesive bandage 20 are bonded together to seal the medical adhesive bandage 20 in between the top and bottom sheets 12 and 14 of the package.

Although the preferred method of bonding the top and bottom sheets 12 and 14 of packaging material is cohesive material as described above, it will be understood that the top and bottom sheets 12 and 14 of packaging material could be sealed around each medical adhesive bandage 20 by any suitable method including heat sealing, adhesives, mechanical bonds, etc. Regardless of the sealing mechanism, it is preferred that it be compatible with sterilization process, e.g., gamma irradiation, ethylene oxide, etc.

It is preferred that one or both of the top sheet 12 and bottom sheet 14 be unattached along one edge to form tabs 13 and 15, respectively, that are not bonded together. Tabs 13 and 15 facilitate separation of the top and bottom sheets 12 and 14 to expose the medical adhesive bandage 20 for removal from the package. As shown, one preferred form of tabs 13 and 15 is formed by folding over a portion of the top and bottom sheets 12 and 14 of packaging material.

Figure 3:
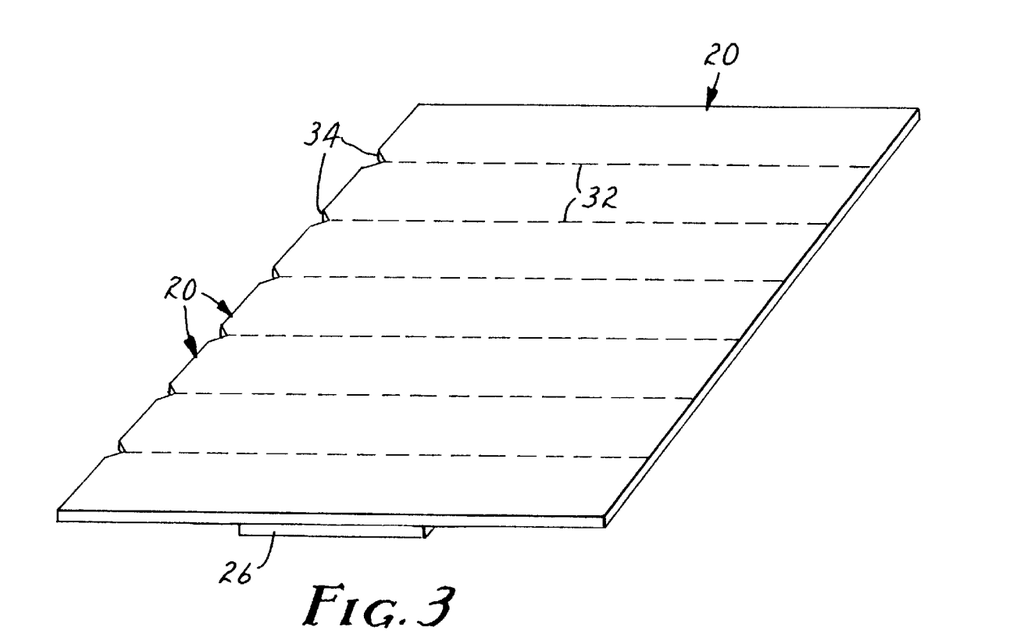
FIG. 3 is a top perspective view of one medical adhesive bandage for use in a medical adhesive bandage delivery system according to the present invention.
Figure 4:
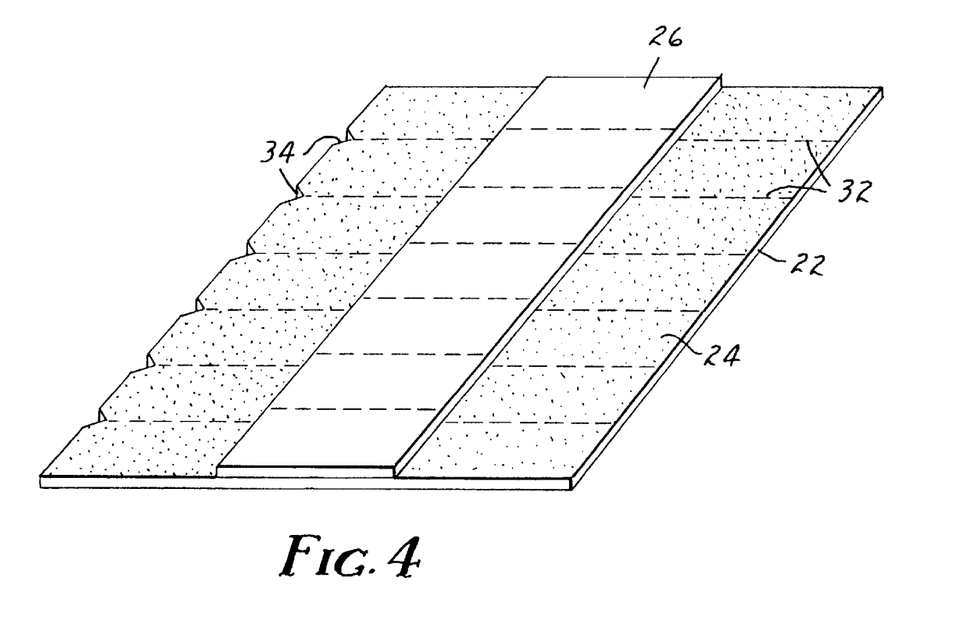
FIG. 4 is a bottom perspective view of the medical adhesive bandage of FIG. 3.

Turning now to FIGS. 3 and 4, the medical adhesive bandage 20 used in the medical adhesive bandage delivery system according to the present invention will be described more completely. The medical adhesive bandage 20 includes a backing 22 as described above. The backing 22 preferably includes an adhesive 24 on a first, or bottom, surface as best seen in FIG. 4. The medical adhesive bandage 20 also includes a pad 26 attached to the first surface of the backing 22. Typically, the pad 26 will be attached to the backing 22 using the adhesive 24, but it may, alternatively, be attached to the backing 22 by any suitable method.

As seen in FIGS. 3 and 4, the pad 26 is preferably centered between the edges of the backing 22 and extends substantially along the length thereof. The pad 26 is typically absorbent, and can be manufactured from a number of materials including but not limited to, woven or nonwoven cotton, rayon, nonwovens, hydrocolloids, foams, and combinations thereof. The pad 26 may also contain a number of substances, including antimicrobial agents, anesthetics, anti-itch agents, drugs for transdermal drug delivery, chemical indicators to monitor hormones or other substances in a patient, combinations thereof and the like. Furthermore, although pad 26 is shown as being generally rectangular and centered on the backing 22, it can take any appropriate shape and/or the pad 26 can be located off-center on the backing 22 as desired.

The medical adhesive bandage 20 of the present invention includes at least one and preferably a plurality of lines of separation 32 as seen in FIGS. 3 and 4. The lines of separation 32 are preferably parallel to each other and extend across the width of the backing 22. The lines of separation 32 are also preferably spaced at regular intervals along the length of the backing 22. The lines of separation 32 can take a number of different forms, provided they allow for relatively clean separation of the medical adhesive bandage 20 into smaller bandages as desired by the user.

One preferred line of separation 32 is a line of perforations separated by land portions as shown in FIGS. 3 and 4. Another example of a line of separation is a line of weakness, i.e., a thinning of the backing 22, that could be molded or otherwise formed in the backing 22 particularly useful with foam and non-woven backings). In some instances, it may be desirable to combine a line of weakness with perforations to ensure clean separation of the medical adhesive bandage 20 into smaller bandages. Some potentially useful constructions for the lines of separation 32 are disclosed in U.S. Pat. No. 5,496,605 to Augst et al. Regardless of the exact construction of the lines of separation 32, it is important that they offer the desired functionality of being relatively easy to tear but typically do not separate when flexed after applied to a patient.

It is also preferred that a notch 34 in the backing 22 be provided on at least one end of each of the lines of separation 32. The notch 34 provides a convenient starting place for separating the medical adhesive bandage 20 into smaller bandages. It also provides a visual reference as to the location of each of the lines of separation 32 for the user when the packaging materials are translucent (which many are) or transparent.

The embodiment of the medical adhesive bandage 20 depicted in FIG. 4 includes a substantially continuous pad 26 that extends along the length of the backing 22. The lines of separation 32 in the backing 22 preferably also extend through the pad 26 as depicted. As a result, tearing or separation of the backing 22 along a line of separation 32 also results in separation of the pad at the desired location.

When the pad 26 is to be torn or separated along a line of separation by a user, it is preferred that the pad 26 be constructed of materials with relatively short fibers to facilitate clean separation of the pad material along the lines of separation 32. Examples of pad materials with relatively short fibers are those based on wood pulp fibers and other materials with fibers having similar lengths. One preferred pad material incorporates wood pulp fibers. Pad weights will typically range up to about 200 grams per square meter, although heavier pad materials can be used if they provide the desired tearability. It is possible, however, to provide pads 26 having longer fibers (such as, e.g., nonwoven polyesters) with the understanding that the edges of the pad material may appear frayed or otherwise uneven where separated by the user.

Figure 5:
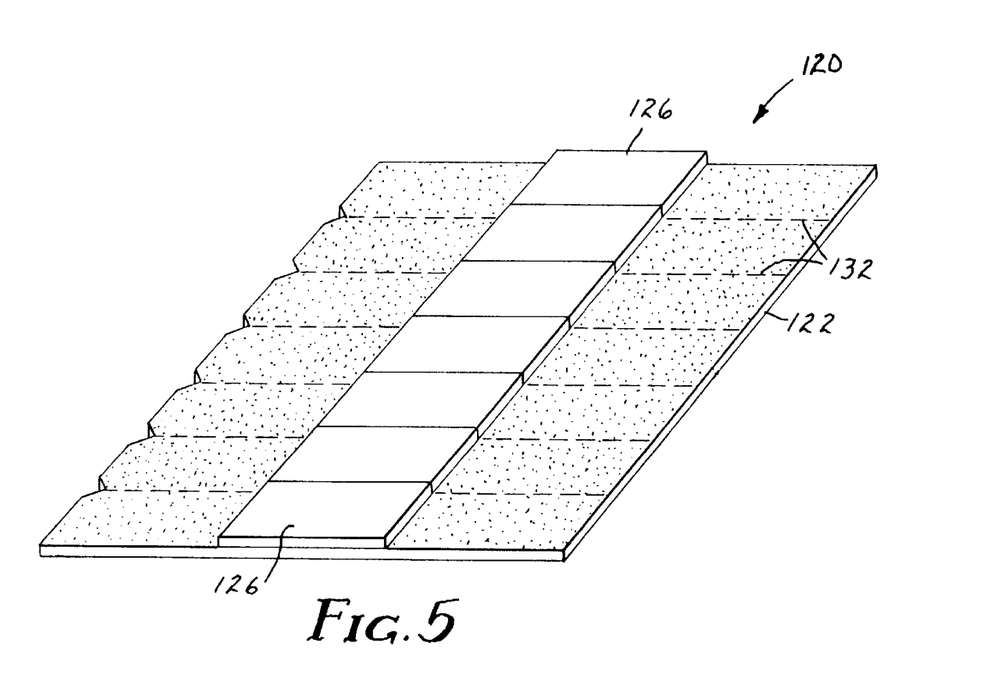
FIG. 5 is a bottom perspective view of another medical adhesive bandage useful in a medical adhesive bandage delivery system according to the present invention.

One alternative to providing a pad 26 with lines of separation 32 is depicted in FIG. 5. The medical adhesive bandage 120 includes a backing 122 with lines of separation 132 formed therein, much in the same manner as described above. The difference between embodiments lies in the pad material used in the medical adhesive bandage 120. Rather than a single pad 26 including fines of separation, the medical adhesive bandage 120 includes a plurality of pads 126. Each pair of adjacent pads 126 preferably meets at one of the lines of separation 132 in the backing 122. As a result, separation of the backing 122 along a line of separation 132 does not require separation of the pad material as described with the embodiment depicted in FIGS. 3 and 4.

The pads 126 may be immediately adjacent each other as shown in FIG. 5 or they may be slightly spaced apart. In one example, the lines of separation are spaced at one centimeter intervals and the pads are 0.9 centimeters wide, resulting in a spacing of about one millimeter between adjacent pads. The spacing between the pads 126 should not be too large, however, to avoid noticeable sagging or distortion of the backing 122 between pads 126. Such sagging or distortion could cause the adhesive on the backing 122 to contact the wound surface.

Figure 6:
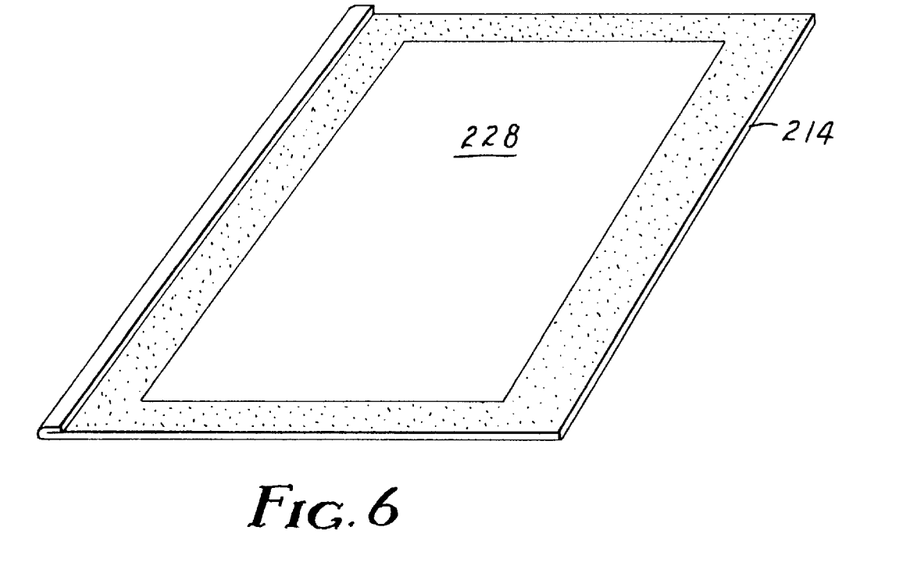
FIG. 6 is a perspective view of a bottom sheet of packaging material including a release area for use in one medical adhesive bandage delivery system according to the present invention.

As indicated with respect to FIG. 1, the medical adhesive bandage 20 includes a liner 28 covering the adhesive 24 on the backing 22. The liner 28 provides a release surface from which the medical adhesive bandage 20 can be removed for placement on a wound site. Referring now to FIG. 6, an alternate embodiment of a bottom sheet 214 of packaging material is depicted including a release area 228. The adhesive of the medical adhesive bandage (not shown) is in contact with the release area 228 when the medical adhesive bandage delivery system 10 of the present invention is manufactured. The release area 228 should be at least as large as the exposed adhesive on the medical adhesive bandage, but may in some instances be larger to simplify attachment and placement of the medical adhesive bandage on the bottom sheet 214 of the packaging material.

Figure 7:
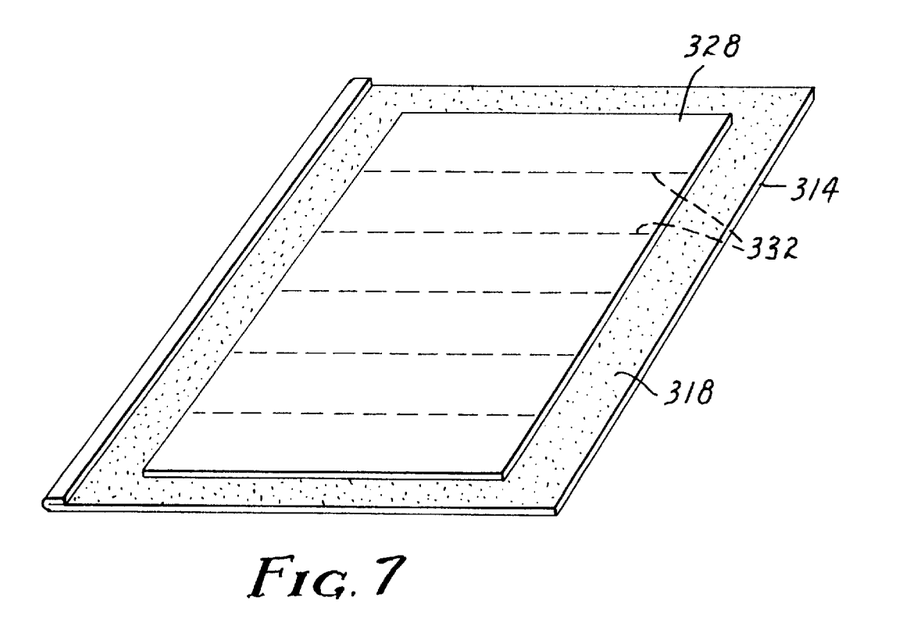
FIG. 7 is a perspective view of an alternative bottom sheet of packaging material including a separate release liner attached thereto for use in one medical adhesive bandage delivery system according to the present invention.

The release area 228 can comprise a release coating on the surface of the bottom sheet 214 or, referring to FIG. 7, release surface can be provided in the form of a separate liner 328 which is itself provided with a release coating. Except as otherwise indicated, the term release area will be used herein to describe either a release coating provided directly on the bottom sheet of the packaging material or a release agent provided on a separate liner attached to the bottom sheet. The separate release liner 328 is attached to the bottom sheet 314 of packaging material with the release surface exposed to bond with the adhesive on the medical adhesive bandage. Typically, the liner 328 would be attached to the medical adhesive bandage first and both the bandage and liner would then be laminated between the top and bottom sheets of the packaging material.

If a separate release liner 328 is provided as release area, it is preferred that the release liner 328 itself include lines of separation 332 located generally beneath each of the lines of separation provided in the medical adhesive bandage as described above. By providing corresponding lines of separation 332 in a separate release liner 328, the tearing of the package and the bandage along relatively straight and clean lines can be facilitated. By providing lines of separation 332 in the release liner 328, coverage of the adhesive on the bandage (and pad) can be maintained after the package is torn because clean separation of the liner 328 is facilitated even if the packaging material does not tear along a straight line.

Also, where the release area is provided as a separate release liner 328 and where the packaging materials are attached using the cohesive material described above, it is preferably attached to the bottom sheet 314 of packaging material using the same cohesive material used to bond the top and bottom sheets of packaging material together. As a result, the release liner 328 preferably includes a layer of the cohesive material on its bottom surface, i.e., the surface facing the bottom sheet 314. That layer of cohesive material bonds to the layer 318 of cohesive material on the bottom sheet 314 of the package. As a result, the medical adhesive bandage (not shown) can be secured in place on the bottom sheet 314. Alternatively, the release liner 328 can be bonded to the bottom sheet 314 of packaging material by any suitable means including, but not limited to: adhesives, mechanical bonds, heat sealing, wax coatings, surface energy attraction, etc.

In a further alternative, the liner 328 may not be attached to the bottom sheet 314 of the packaging material. In that embodiment, the liner 328 would be attached only to the bandage (not shown in FIG. 7). If the liner 328 is attached only to the bandage, the bandage backing and top sheet of the packaging material should combine to provide a tendency for the package to retain the bandage between the top and bottom sheets of the package during and after tearing of the bandage along one of the lines of separation. Typically, the tendency to retain the bandage will be provided by interaction between the cohesive material on the top sheet (see, e.g., FIG. 1) and the backing 22.

Regardless of the actual mechanism used to provide a release area 228 on the bottom sheet 214 of packaging material, the bond between the release area 228 and the bottom sheet 214 of the package material should be stronger than the bond between the adhesive of the medical adhesive bandage and the release area 228 to ensure easy and consistent removal of the medical adhesive bandage from the bottom sheet 214 of the package.

Figure 2:
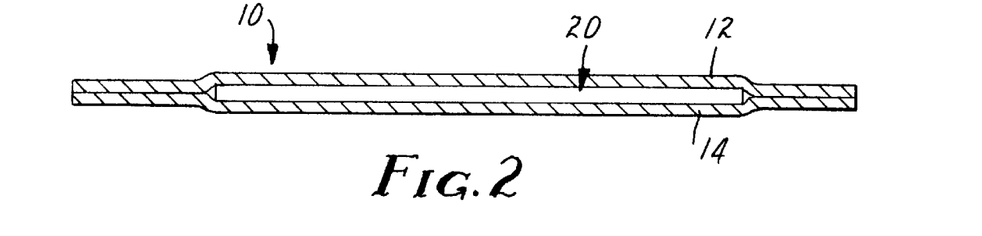
FIG. 2 is a cross-sectional view of the medical adhesive bandage delivery system of FIG. 1 as assembled.
Figure 8:
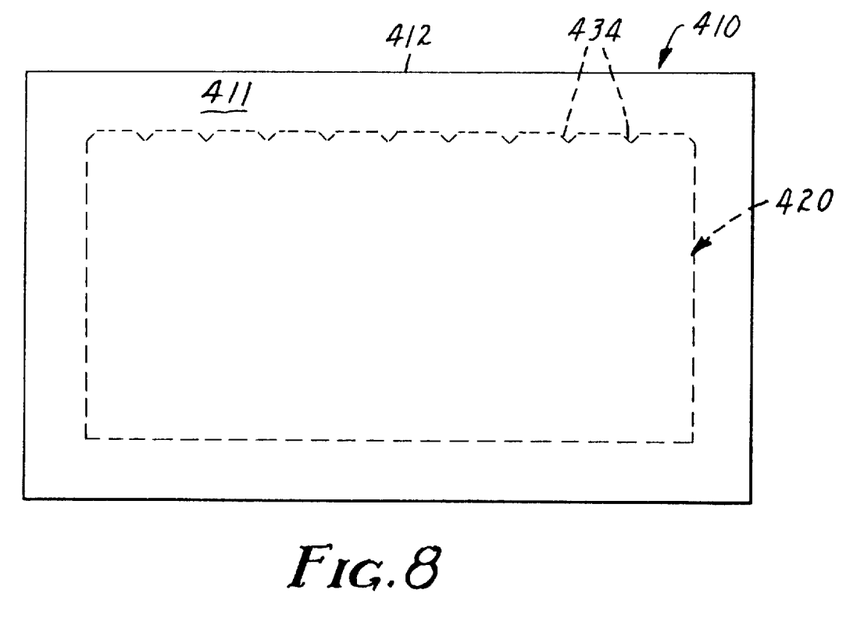
FIG. 8 is a plan view of one medical adhesive bandage delivery system according to the present invention.

Turning now to FIGS. 8–11, one method of using a medical adhesive bandage delivery system according to the present invention will be described. The method begins with providing a medical adhesive bandage delivery system 410 as shown in FIG. 8. The medical adhesive bandage delivery system 410 is provided in the form of a sheet medical adhesive bandage 420 enclosed in the top and bottom sheets of a package as described above in connection with FIGS. 1 and 2. The medical adhesive bandage 420 is depicted in hidden lines as it will be understood that the medical adhesive bandage 420 will be obscured by the top sheet 412 of the packaging material. As shown the area 411 of the packaging material surrounding the enclosed medical adhesive bandage 420 provides a seal to prevent contamination of the medical adhesive bandage 420 before the package is opened.

Figure 9:
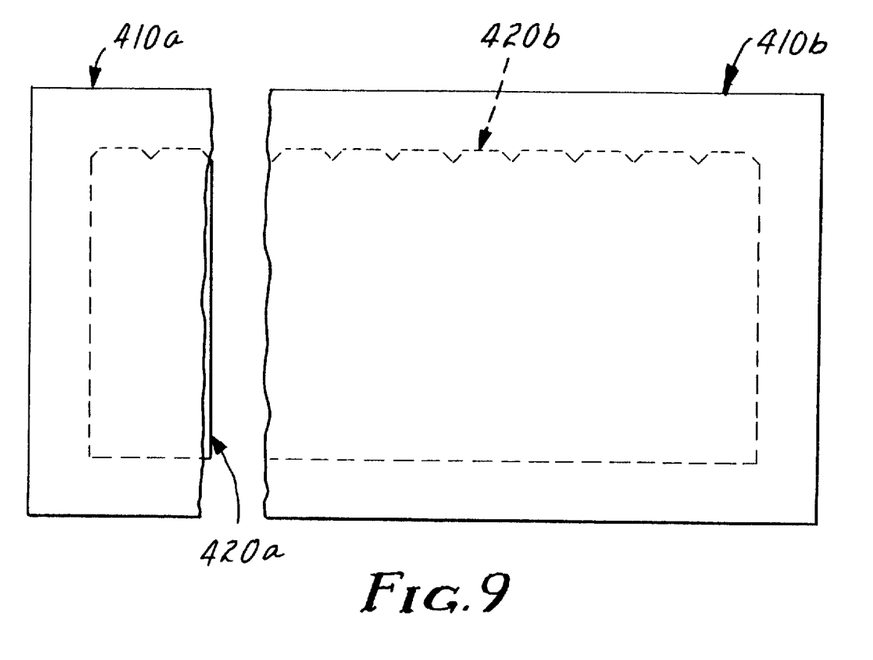
FIG. 9 is a plan view of the medical adhesive bandage delivery system of FIG. 8 after separation of the medical adhesive bandage delivery system into two portions.

Turning now to FIG. 9, the medical adhesive bandage delivery system 410 is separated into two portions 410a and 410b, each of which contains a portion of the medical adhesive bandage 420a or 420b as shown. The medical adhesive bandage 420 is preferably separated along one of the lines of separation that is indicated by each of the notches 434 in FIG. 8. The separation can preferably be accomplished by tearing the medical adhesive bandage delivery system 410, although it would also be possible to effect the separation by use of a scissors or other cutting instrument. At this point either of the medical adhesive bandages 420a or 420b can be removed from the package and applied over a wound.

One feature and advantage of the present invention is that both portions of the medical adhesive bandage 420a and 420b will be retained within the packaging material after the separation step has been performed. Retention of the medical adhesive bandage within the packaging material provides increased levels of protection for the unused portion of the medical adhesive bandage, which can then be stored for future use while limiting exposure of the pad and adhesive to undesirable debris.

Figure 10:
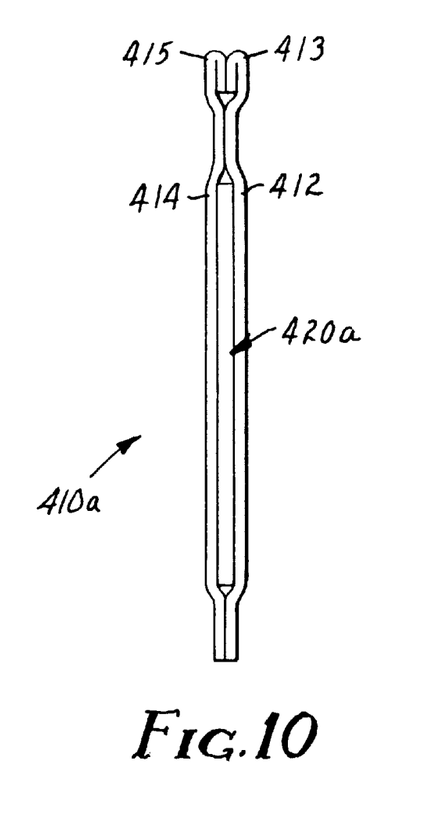
FIG. 10 is a side view of the step of separating the packaging material to deliver a medical adhesive bandage in one method according to the present invention.

Turning to FIG. 10, the portion 410a of the medical adhesive bandage delivery system is opened to dispense the medical adhesive bandage 420a by separating the top sheet 412 of packaging material from the bottom sheet 414 of packaging material. Typically, the top and bottom sheets 412 and 414 will be provided with tabs 413 and 415 to facilitate separation of the packaging material.

Figure 11:
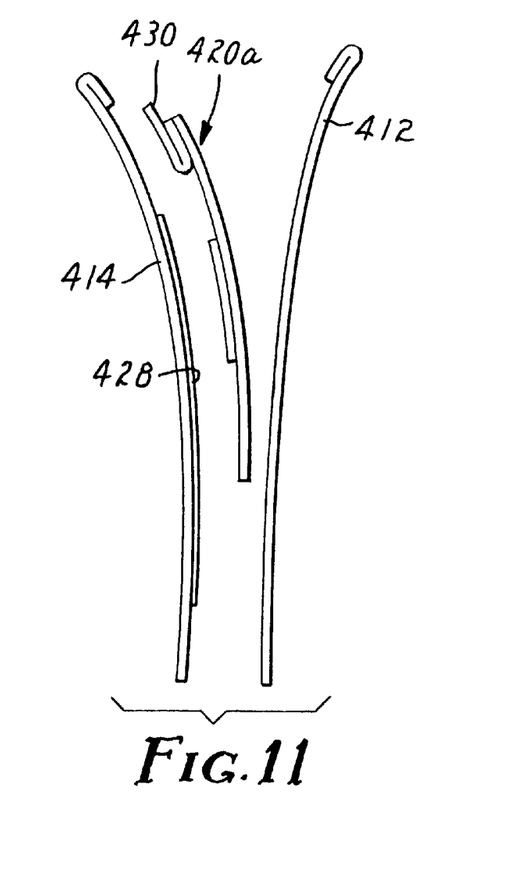
FIG. 11 is a side view of the step of removing the medical adhesive bandage from the package in one method according to the present invention.

After the medical adhesive bandage 420a is exposed by separation of the top sheet 412 from the bottom sheet 414 it can be removed from the release liner 428 as depicted in FIG. 11. As discussed with the earlier-described embodiments, the release liner 428 is preferably attached to the bottom sheet 414 of the packaging material. As a result, the user can grasp the portion of the bandage 420a covered by the (optional) release tab 430 to remove the medical adhesive bandage 420a from the liner 428 so that it can be applied over wound (after which the tab 430 can be removed if desired).

Although the medical adhesive bandage delivery systems of the present invention has been depicted as having from 6–9 lines of separation in the backing, it will be understood that the medical adhesive bandages of the present invention can have as few as one line of separation. Similarly, the medical adhesive bandages may have 10 or more lines of separation (up to any desired number). It may be advantageous to provide the medical adhesive bandage delivery system in roll-form if the length of the medical adhesive bandage is longer than convenient to provide in sheet form. If provided in roll-form, the packaging material essentially forms an elongated sleeve to protect the unused portion of the medical adhesive bandage.

Also, although the medical adhesive bandages have been described above as provided as a single bandage having at least one line of separation, those skilled in the art will understand that, alternatively, the present invention can also be characterized as a plurality of bandages connected to each other along the same line or lines of separation. If characterized in this fashion, i.e., a plurality of connected bandages, then the pads of each of the bandages can be either connected along their own lines of separation (see, e.g., pad 26 in FIG. 4) or provided as separate, but aligned pads (see, e.g., pads 126 in FIG. 5). Regardless of the characterization, the present invention provides a delivery system for and method of delivering medical adhesive bandages of varying lengths while retaining any unused portion in a relatively clean package for later use.

The following non-limiting example is provided to illustrate one embodiment of the invention described above and is not intended to limit the scope of the present invention, which is defined by the claims appended hereto.

EXAMPLE

A medical adhesive bandage delivery system according to the present invention was assembled with the following components:

The packaging material for the top and bottom sheets was a 25 pound (41 grams per square meter) Rhinelander medical kraft paper coated with a cohesive material from Phoenix Products Company, Inc. Milwaukee, Wis.).

The release liner was the same packaging material used for the top and bottom sheets, but coated on one side with Goldschmidt silicone (Goldschmidt Chemical Corp., Hopewell, Va.) and on the other side with the cohesive material used on the packaging material. The release tab material was ESP 48 silicone-coated paper supplied by Daubert Coated Products, Inc. (Willowbrook, Ill.).

The backing for the medical adhesive bandage was 105 grams per square meter urethane nonwoven made as specified in U.S. Pat. No. 5,230,701 to Meyer et al. from Morton PS440-200 polyurethane material available from Morton International, Inc. (Seabrook, N.H.).

The adhesive used was a tackified acrylate as discussed in U.S. Pat. No. 4,112,177 (Example 1, "skin layer adhesive"). The adhesive was coated on the backing at a weight of 50 grams per square meter.

The pad material was wood pulp fiber based and had a weight of 111 grams per square meter and is available from Applied Extrusion Technologies, Inc., Middletown Del. under the designation CKX215/SH3116-.6/WS-FG403.

The backing, pad, and release liner materials were all perforated to form the lines of separation. The perforations were 2.4 mm long (3/32 inches) and spaced about 0.8 mm apart (1/32 inches).

The components were assembled as shown in FIG. 1 to form a medical adhesive bandage in an envelope of two sheets of packaging material.

All patents, patent applications, and publications cited herein are each incorporated herein by reference in their entirety, as if individually incorporated by reference. Various modifications and alterations of this invention will become apparent to those skilled in the art without departing from the scope of this invention, and it should be understood that this invention is not to be unduly limited to the illustrative embodiments set forth herein.

What is claimed is:

1. A medical adhesive bandage comprising:
    a backing having a first surface;
    an adhesive on the first surface of the backing;
    a pad on the first surface of the backing;
    at least one line of separation in the backing and pad to facilitate selective manual separation of the bandage into at least two smaller bandages; and
    a notch formed in the backing at an end of the at least one line of separation.

2. A medical adhesive bandage according to claim 1 wherein the backing is formed of a nonwoven elastomeric material.

3. A medical adhesive bandage according to claim 2 wherein the elastomeric material comprises polymerized units of urethane.

4. A medical adhesive bandage according to claim 1 further comprising a release liner releasably affixed to the adhesive on the first surface of the backing, the line of separation being further formed in the release liner.

5. A medical adhesive bandage according to claim 4 wherein the line of separation comprises a line of perforations through the backing and release liner, with a plurality of lands separating adjacent perforations.

6. A combination of the medical adhesive bandage according to claim 4 with packaging comprising a bottom sheet and a top sheet sealed together along their periphery with the bandage inside, the package tending to retain the medical adhesive bandage therein when the package is torn and the bandage separated along the line of separation.

7. A medical adhesive bandage delivery system comprising:
    a medical adhesive bandage comprising:
        a backing;
        an adhesive on a first surface of the backing;
        a pad proximate the first surface of the backing;
        at least one line of separation in the backing and the pad to facilitate selective manual separation of the bandage into at least two smaller bandages; and
    a package comprising:
        a top sheet having an inner surface and an outer surface;
        a bottom sheet having an inner surface and an outer surface; and
        a release area on the inner surface of the bottom sheet of the package, wherein the adhesive on the medical adhesive bandage is releasably adhered to the release area.

8. A system according to claim 7, comprising at least two lines of separation in the backing and pad.

9. A system according to claim 7, wherein the at least one line of separation comprises a line of perforations.

10. A system according to claim 7, further comprising a notch formed in the backing at an end of the at least one line of separation.

11. A system according to claim 7, wherein the release area comprises a release coating on the inner surface of the bottom sheet.

12. A system according to claim 7, wherein the release area comprises a release liner attached to the inner surface of the bottom sheet.

13. A system according to claim 12, wherein the release liner comprises at least one line of separation formed therein.

14. A system according to claim 12, wherein the bond strength between the release liner and the inner surface of the bottom sheet is greater than the bond strength between the adhesive on the medical adhesive bandage and the release liner.

15. A medical adhesive bandage delivery system comprising:
    a medical adhesive bandage comprising:
        a backing;
        an adhesive on a first surface of the backing;
        a pad proximate the first surface of the backing;
        at least one line of perforations in the backing and the pad to facilitate selective manual separation of the bandage into more than one bandage; and
    a package comprising:
        a top sheet having an inner surface and an outer surface;
        a bottom sheet having an inner surface and an outer surface; and
        a release liner attached to the inner surface of the bottom sheet of the package, the release liner including at least one line of separation formed therein, wherein the bond strength between the release liner and the inner surface of the bottom sheet is greater than the bond strength between the adhesive on the medical adhesive bandage and the release liner.

16. A medical adhesive bandage delivery system comprising:
    a medical adhesive bandage comprising:
        a backing;
        an adhesive on a first surface of the backing;
        a plurality of pads proximate the first surface of the backing, the plurality of pads being generally aligned along a length of the backing; and at least one line of separation located in the backing between adjacent pads; and a package comprising:
- a top sheet having an inner surface and an outer surface;
- a bottom sheet having an inner surface and an outer surface; and
- a release area on the inner surface of the bottom sheet of the package, wherein the adhesive on the medical adhesive bandage is releasably adhered to the release area.

17. A system according to claim 16, wherein adjacent pairs of the plurality of pads are immediately adjacent each other.

18. A system according to claim 16, comprising at least two lines of separation in the backing.

19. A system according to claim 16, wherein the at least one line of separation comprises a line of perforations.

20. A system according to claim 16, further comprising a notch formed in the backing at an end of the at least one line of separation.

21. A system according to claim 16, wherein the release area comprises a release coating on the inner surface of the bottom sheet.

22. A system according to claim 16, wherein the release area comprises a release liner attached to the inner surface of the bottom sheet.

23. A system according to claim 22, wherein the release liner comprises at least one line of separation formed therein.

24. A system according to claim 22, wherein the bond strength between the release liner and the inner surface of the bottom sheet is greater than the bond strength between the adhesive on the medical adhesive bandage and the release liner.

25. A system according to claim 16, wherein at least one of the top and bottom sheets of the package comprises an oriented fiber paper, whereby tearing of the package along each of the at least one lines of separation in the medical adhesive bandage is facilitated.

26. A medical adhesive bandage delivery system comprising:

a medical adhesive bandage comprising:
- a backing;
- an adhesive on a first surface of the backing;
- at least one line of perforations in the backing; and
- a plurality of pads proximate the first surface of the backing, the plurality of pads being generally aligned along a length of the backing, wherein one of the at least one line of perforation is located between each adjacent pair of the plurality of pads; and a package comprising:
- a top sheet having an inner surface and an outer surface;
- a bottom sheet having an inner surface and an outer surface; and
- a release liner on the inner surface of the bottom sheet of the package, the release liner including at least one line of perforations formed therein, wherein the bond strength between the release liner and the inner surface of the bottom sheet is greater than the bond strength between the adhesive on the medical adhesive bandage and the release liner.

27. A method of delivering a medical adhesive bandage comprising steps of:

providing a medical adhesive bandage delivery system comprising a medical adhesive bandage having a backing; an adhesive on a first surface of the backing; a pad proximate the first surface of the backing; and at least one line of separation in the backing and the pad; wherein the medical adhesive bandage is packaged in a package comprising a top sheet having an inner surface and an outer surface; a bottom sheet having an inner surface and an outer surface; and a release area on the inner surface of the bottom sheet of the package, wherein the adhesive on the medical adhesive bandage is releasably adhered to the release area;

separating the package and the medical adhesive bandage along one of the at least one line of separation in the medical adhesive bandage, whereby the medical adhesive bandage delivery system is separated into first and second portions;

separating the top and bottom sheets of the package in the first portion of the medical adhesive bandage delivery system; and removing the medical adhesive bandage from the release area on the bottom sheet of the package in the first portion of the medical adhesive bandage delivery system.

28. A method according to claim 27, wherein the medical adhesive bandage in the second portion of the medical adhesive bandage delivery system is retained between the top and bottom sheets of the package in the second portion of the medical adhesive bandage delivery system.

29. A method according to claim 27, further comprising steps of:

grasping the second portion of the medical adhesive bandage delivery system;

tearing the package and the medical adhesive bandage of the second portion of the medical adhesive bandage delivery system along one of the at least one line of separation in the medical adhesive bandage, whereby the second portion of the medical adhesive bandage delivery system is separated into third and fourth portions;

separating the top and bottom sheets of the package in the third portion of the medical adhesive bandage delivery system; and removing the medical adhesive bandage from the release area on the bottom sheet of the package in the third portion of the medical adhesive bandage delivery system.

30. A medical adhesive bandage delivery system comprising:

a sheet comprising a plurality of medical adhesive bandages, each of the plurality of medical adhesive bandages comprising a backing, adhesive on a first surface of the backing, and a pad proximate the first surface of the backing, wherein adjacent pairs of the plurality of medical adhesive bandages are connected along a line of separation;

a top sheet of packaging material having an inner surface and an outer surface;

a bottom sheet of packaging material having an inner surface and an outer surface; and a release area on the inner surface of the bottom sheet of the packaging material, wherein the adhesive on each of the plurality of medical adhesive bandages is releasably adhered to the release area.

31. A system according to claim 30, wherein the line of separation between each of the adjacent pairs of the plurality of bandages comprises a line of perforations.

32. A system according to claim 30, wherein the pads between each of the adjacent pairs of the plurality of bandages are connected along a line of separation.

33. A system according to claim 32, wherein the line of separation between the pads on each of the adjacent pairs of the plurality of bandages comprises a line of perforations.

34. A system according to claim 30, wherein the release area comprises a release coating on the inner surface of the bottom sheet.

35. A system according to claim 30, wherein the release area comprises a release liner attached to the inner surface of the bottom sheet.

36. A system according to claim 35, wherein the release liner comprises at least one line of separation formed therein.

37. A system according to claim 35, wherein the bond strength between the release liner and the inner surface of the bottom sheet is greater than the bond strength between the adhesive on each of the plurality of medical adhesive bandages and the release liner.

38. A combination of a medical adhesive bandage and packaging, the combination comprising:
- a medical adhesive bandage comprising:
  - a backing having a first surface;
  - an adhesive on the first surface of the backing;
  - a pad on the first surface of the backing;
  - a release liner releasably affixed to the adhesive on the first surface of the backing; and
  - at least one line of separation in the backing, the pad and the release liner to facilitate selective manual separation of the bandage into at least two smaller bandages; and
- packaging comprising a bottom sheet and a top sheet sealed together along their periphery with the bandage inside, the package tending to retain the medical adhesive bandage therein when the package is torn and the bandage is separated along the line of separation.

39. A combination according to claim 38, wherein the backing is formed of a nonwoven elastomeric material.

40. A combination according to claim 39, wherein the elastomeric material comprises polymerized units of urethane.

41. A combination according to claim 38, wherein the line of separation comprises a line of perforations through the backing and release liner, with a plurality of lands separating adjacent perforations.

42. A combination of a medical adhesive bandage and a package, the combination comprising:
- a medical adhesive bandage comprising:
  - a backing having a first surface;
  - an adhesive on the first surface of the backing;
  - a pad on the first surface of the backing;
  - a release liner releasably affixed to the adhesive on the first surface of the backing;
  - at least one line of separation in the backing, release liner and pad to facilitate selective manual separation of the bandage into at least two smaller bandages;
  - a notch formed in the backing at an end of the at least one line of separation; and
- a package comprising a bottom sheet and a top sheet sealed together along their periphery with the bandage inside, the package tending to retain the medical adhesive bandage therein when the package is torn and the bandage separated along the line of separation.

43. A combination according to claim 42, wherein the backing is formed of a nonwoven elastomeric material.

44. A combination according to claim 43, wherein the elastomeric material comprises polymerized units of urethane.

* * * * *

UNITED STATES PATENT AND TRADEMARK OFFICE
CERTIFICATE OF CORRECTION

PATENT NO. : 6,018,092
APPLICATION NO. : 08/810584
DATED : January 25, 2000
INVENTOR(S) : Wayne K. Dunshee Page 1 of 1

It is certified that error appears in the above-identified patent and that said Letters Patent is hereby corrected as shown below:

On title page please add the following references:

-- Pamphlet "Tegaderm TM Transparent Dressing, suggested Applications & Special Techniques"; 3M Health Care, October 1991--

--Pamphlet "Tegaderm TM Transport Dressing, The clear Choice for easier application and improved patient care"; 3M Health Care; 1994.--

--"Bertek Research & Development, Manufacturing, Transdermal Health Carem Wound Care" 1991 Bertek, Inc.--

--Article, San Francisco Examiner, "Patents: A new, better bandage"; Tuesday, March 28, 1995.--

--Chapter 18 of the Handbook of Pressure-Sensitive Adhesive Technology, Van Nostrand Reinhold Company, 1982, pp. 384-403.--

Signed and Sealed this

Seventeenth Day of July, 2007

JON W. DUDAS
*Director of the United States Patent and Trademark Office*